Jan. 12, 1937. A. F. J. BAUR Plant Pat. 219
CARNATION
Filed July 29, 1936
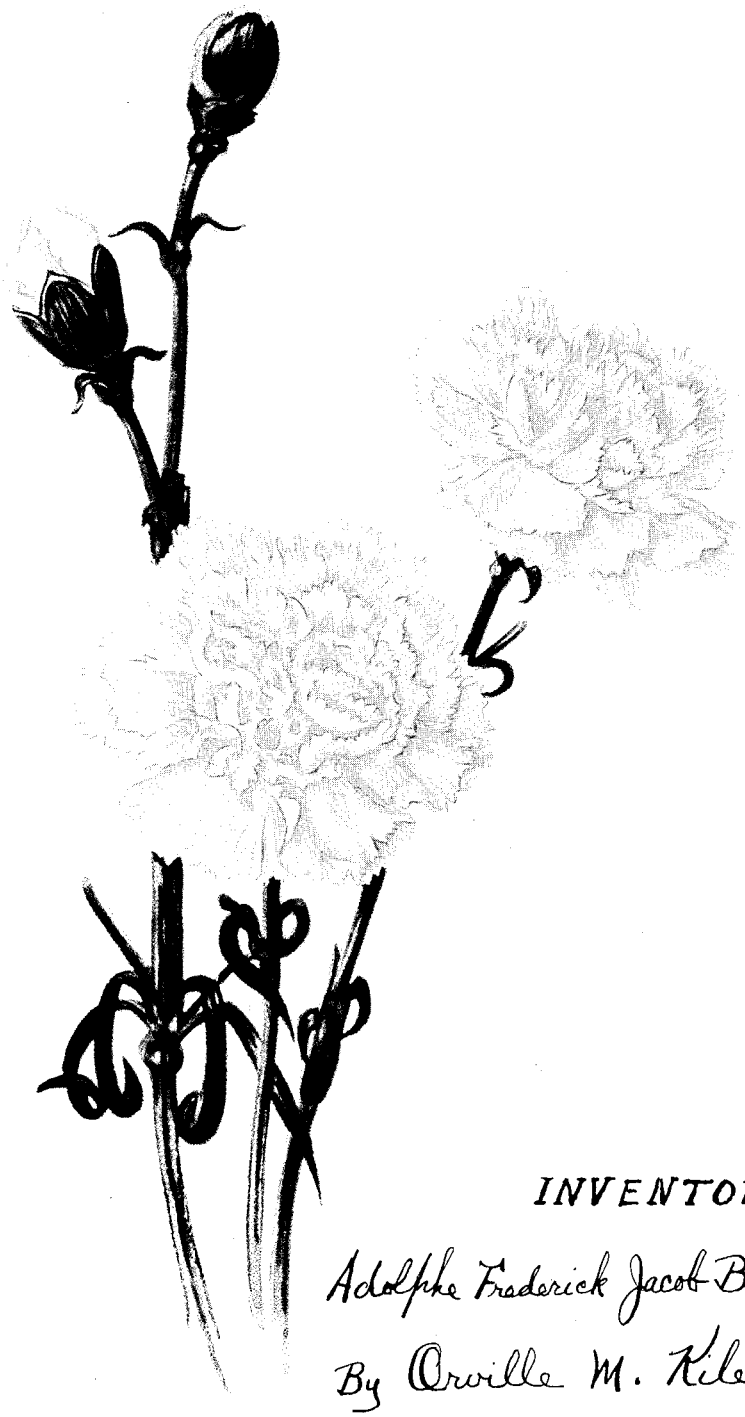
INVENTOR
Adolphe Frederick Jacob Baur
By Orville M. Kile
Plant Patent Agent.

Patented Jan. 12, 1937

Plant Pat. 219

UNITED STATES PATENT OFFICE

219

CARNATION

Adolphe Frederick Jacob Baur, Indianapolis, Ind., assignor to Baur-Steinkamp and Company, Incorporated, Indianapolis, Ind.

Application July 29, 1936, Serial No. 93,294

1 Claim. (Cl. 47—60)

My invention relates to improvements in medium pink carnations ordinarily known as greenhouse forcing carnations. The object of my invention is to produce a pink variety of carnation comparable to the white variety Patrician in all-round excellence.

This variety is a cross between two numbered but unnamed and undisseminated seedlings, the cross having been made in 1931. The female parent is also the female parent of Patrician.

The original illustrations accompanying this application show in full color two blossoms and two buds in varying stages of opening, together with stems and foliage, as they appear in the month of March. It must be understood, however, that allowance must be made for differences in color because of variation of seasons, climate and other conditions.

The following is a detailed description of this variety and the color references are to Ridgway's Color Standards and Nomenclature.

*The plant*

*Habit of growth.*—Sturdy; spreading; propagates easily and blooms very freely.

*Stems.*—Very strong; medium length.

*Color.*—Elm green (Plate XVII) with light gray bloom.

*Nodes.*—Prominent.

*Foliage.*—Long and narrow leaves; only slightly curled; ample but not "grassy."

*Color.*—Same as stem.

*Calyx.*—Long, tough, non-splitting, five-lobed.

*Color (of calyx).*—Top, oil green (Pate V); base, cosse green (Plate V).

*Size.*—Large—1½ inch long by 1¼ inch wide.

*Bracts.*—Strong and well developed; points have same color as the stems; base much lighter green.

*The flower*

*Bud.*—Longer than usual for the number of petals.

Flower:

*Size.*—Very large and full—3½ to 4 inches across in the winter and early spring months.

*Shape.*—Relatively regular.

*Petalage.*—Large number of petals—70 to 75 in the month of June (about 35 large, 28 medium, 10 small).

*Petals.*—Outer petals measure about 1¼ inches in width. Central petals much smaller and somewhat shorter. Serrations pronounced, some rather deep. Medium heavy texture. Closely folded and curled in center of flower.

*Fragrance.*—Very strong but pleasant cinnamon odor.

*Longevity.*—Keeping qualities as a cut flower are excellent.

*Color.*—Ridgway's Color Standards and Nomenclature does not give a color which describes this variety. The nearest approach is between rose color and rose red (Plate XII), although there is considerably more brilliance and a slight carrot red toning of this color. The coloring is spread rather evenly over the individual petals. However the under side of the petals is of a lighter hue and, due to the folding and crinkling of the petals, two tones are distinctly noticed in the flower.

*Reproductive organs*

*Stamens.*—Long; white; uneven length; about 25.

*Anthers.*—Buff colored; small; arise from pithy ring at base of ovary—outer ones often attached to petals at base.

*Ovary.*—Three-lobed; large and high; contains many ovules; cover very tough.

*Styles.*—Two or three white, very long and heavy styles arise from the top of the high ovary in spreading formation, extending above the stamens and often above the petals. These styles are of unusual appearance. The lower inch is very broad (⅛ inch) and is formed of two segments with a groove down the center between them. At the base and point of attachment to the ovary these two segments are folded entirely together but progressing upward these segments open more nearly flat. At the top of these two segments are found little spurs or rudimentary branches. Arising from the center or groove of this broad portion of the style and flanked on each side by the spurs, is a small round portion about ¼ inch long, which curls backward from the groove.

*Comparisons*

The carnation most nearly like this new variety is the Rose Charm, the subject of Plant Patent No. 133. The new variety differs from Rose Charm, however, in several very important respects, among which are the following:

1. The new variety has a much longer bud.
2. It is less inclined to split the calyx.
3. It blooms more steadily and freely.
4. It has a much stronger stem.
5. It is of less compact and stronger growth.
6. It has a greater number of petals.

7. The color is more evenly spread to the edge of the petals and is a trifle brighter, with a little less of the salmon tone.

8. It has much wider and longer styles.

9. Its petal serrations are greater.

10. Its foliage is grayer.

The new variety grows somewhat less compactly than Rose Charm, its growth characteristics being more like those of Patrician, although it grows about 20 percent taller than Patrician. Its leaves are narrower and have slightly more gray color than those of Patrician.

Having thus disclosed my invention, I claim:

The variety of fragrant, medium pink carnation as shown and described, characterized particularly by its large flowers of distinctive coloring as described, its vigorous growth, its free and steady blooming, its strong stems and its strong non-splitting calyx.

ADOLPHE FREDERICK JACOB BAUR.